United States Patent
Laakkonen et al.

(10) Patent No.: US 9,675,267 B2
(45) Date of Patent: Jun. 13, 2017

(54) DEVICE FOR PHYSIOLOGICAL MEASUREMENT

(71) Applicant: FIRSTBEAT TECHNOLOGIES OY, Jyväskylä (FI)

(72) Inventors: Kauko Laakkonen, Jyväskylä (FI); Toni Järvitalo, Jyväskylä (FI); Aku Kalajo, Jyväskylä (FI); Sami Saalasti, Jyväskylä (FI)

(73) Assignee: Firstbeat Technologies Oy, Jyväskylä (FI)

( * ) Notice: Subject to any disclaimer, the term of this patent is extended or adjusted under 35 U.S.C. 154(b) by 0 days.

(21) Appl. No.: 14/436,423

(22) PCT Filed: Oct. 31, 2013

(86) PCT No.: PCT/FI2013/051035
§ 371 (c)(1),
(2) Date: Apr. 16, 2015

(87) PCT Pub. No.: WO2014/068193
PCT Pub. Date: May 8, 2014

(65) Prior Publication Data
US 2015/0272466 A1  Oct. 1, 2015

Related U.S. Application Data

(60) Provisional application No. 61/738,420, filed on Dec. 18, 2012.

(30) Foreign Application Priority Data

Oct. 31, 2012 (FI) .................................. 20126140

(51) Int. Cl.
*A61B 5/04* (2006.01)
*A61B 5/0428* (2006.01)
(Continued)

(52) U.S. Cl.
CPC ........ *A61B 5/04288* (2013.01); *A61B 5/0245* (2013.01); *A61B 5/02438* (2013.01);
(Continued)

(58) Field of Classification Search
CPC . A61B 5/0416; A61B 5/04325; A61B 5/0408; A61B 5/04288; A61B 5/0006;
(Continued)

(56) References Cited

U.S. PATENT DOCUMENTS 6,117,077 A * 9/2000 Del Mar ............ A61B 5/04085
600/300
6,647,286 B1  11/2003 Kato et al.
(Continued)

FOREIGN PATENT DOCUMENTS

EP   0552009 A1   7/1993
GB   2463784 A    3/2010
(Continued)

OTHER PUBLICATIONS

International Search Report dated May 14, 2014 from corresponding International Patent Application No. PCT/FI2013/051035; 10 pages.
(Continued)

*Primary Examiner* — Mallika D Fairchild
(74) *Attorney, Agent, or Firm* — Maier & Maier, PLLC

(57) ABSTRACT

A device for physiological measurement. The device includes at least two terminal units connectable to each other, of which a first terminal unit includes an electric circuit, an ECG-electrode and a first connector assembly having at least one ECG-contact for connecting at least one other ECG-electrode. A second terminal unit includes other ECG-electrodes and a second connector assembly having a counter ECG-contact adapted to be fitted to the ECG-contact of the first connector assembly. The first and second terminal are together arranged to connect the ECG-electrode of each second terminal unit to the electric circuit in the first terminal unit and, as separated, are arranged to enable the use of the function contacts of the first connector assembly.

9 Claims, 9 Drawing Sheets

Figure 1:
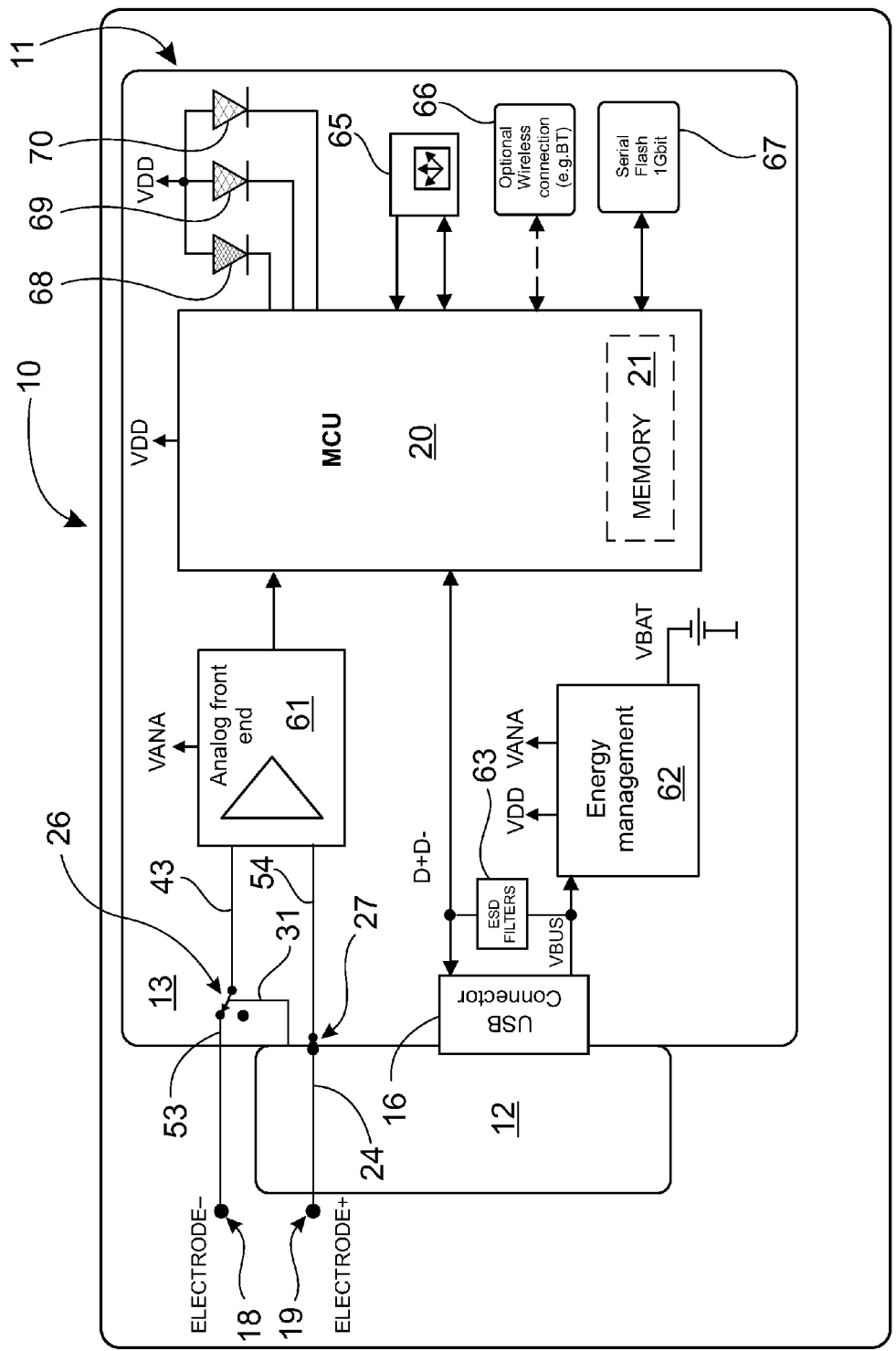

(51) Int. Cl.
  *A61B 5/0416* (2006.01)
  *A61B 5/0432* (2006.01)
  *A61B 5/0408* (2006.01)
  *A61B 5/024* (2006.01)
  *A61B 5/0245* (2006.01)

(52) U.S. Cl.
  CPC .......... *A61B 5/0408* (2013.01); *A61B 5/0416* (2013.01); *A61B 5/04325* (2013.01); *A61B 2562/227* (2013.01)

(58) Field of Classification Search
  CPC ............ A61B 5/040825; A61B 5/0452; A61B 5/02438; A61B 5/0245; A61B 2562/227
  See application file for complete search history.

(56) References Cited

U.S. PATENT DOCUMENTS

| | | |
|---|---|---|
| 6,856,832 B1 | 2/2005 | Matsumura et al. |
| 2004/0077954 A1* | 4/2004 | Oakley ................ A61B 5/0006 600/483 |
| 2007/0027388 A1 | 2/2007 | Chou |
| 2011/0009729 A1 | 1/2011 | Shin et al. |
| 2012/0029299 A1* | 2/2012 | DeRemer ............. A61B 5/0002 600/300 |
| 2012/0110226 A1 | 5/2012 | Vlach et al. |
| 2012/0197144 A1 | 8/2012 | Christ et al. |
| 2012/0257698 A1 | 10/2012 | Zhang |
| 2014/0073982 A1 | 3/2014 | Yang et al. |

FOREIGN PATENT DOCUMENTS

| | | |
|---|---|---|
| WO | 2004034896 A1 | 4/2004 |
| WO | 2004086967 A1 | 10/2004 |
| WO | 2007083314 A2 | 7/2007 |
| WO | 2009134826 A1 | 11/2009 |
| WO | 2010077997 A2 | 7/2010 |
| WO | 2012106086 A1 | 8/2012 |

OTHER PUBLICATIONS

International Preliminary Report on Patentability dated Jan. 21, 2015 corresponding International Patent Application No. PCT/FI2013/051035; 18 pages.

* cited by examiner

Section A - A

Fig. 7b   Section A - A

Section B - B

DEVICE FOR PHYSIOLOGICAL MEASUREMENT

This application claims benefit of priority from International Patent Application No: PCT/FI2013/051035 filed Oct. 31, 2013, which claims benefit of Finland Patent Application No. 20126140 and U.S. Patent application 61/738,420, which all are incorporated by reference in their entirety.

The present invention relates to a device for physiological measurement including
- an electric circuit,
- at least two ECG-electrodes coupled to the electric circuit for measuring heart beats,
- signal processing means assembled in the electric circuit,
- a battery coupled to the electric circuit,
- a connector assembly including function contacts for communication with an external device and/or charging the battery.

Firstbeat Assessment service provides information on the user's stress, recovery, sleep and physical activity related issues. The service includes a measurement of heart rate and the collected data is used as core component while providing the service (data analysis, reports, feedback).

The known devices for measuring heart rate include at least two electrodes. The device enclosure has fixed positions for the electrodes. Due to this reason the electrodes will be placed on the fixed positions when the user is wearing the device on his/hers body.

In addition, the exporting of the heart rate data from the measurement device to the external device and/or the charging of the battery of the measurement device may require function contacts to be in the device. Relating to these may arise the electrical safety problems if an unexperienced user of the device connects the device to the external device and/or charging when he/she is still wearing the device at the same time.

The present invention is intended to create a device for physiological measurement, which has an improved fitting features and improved electrical safety features. The characteristic features of the device according to the invention are presented in Claim 1.

The device includes at least two terminal units connectable to each other each unit having at least one ECG-electrodes. Owing to this relative free placing of the ECG-electrodes is possible. In addition, the units as connected together are arranged to connect the ECG-electrode of each opposite terminal unit to the electric circuit in the first terminal unit and as separated are arranged to enable the use of the function contacts of the first connector assembly. This improves the electrical safety properties of the device. Owing to this it is not possible to connect the measurement device to the external device and/or charging when the units are connected in the measuring mode.

According to one embodiment the terminal units as separated are also arranged to disconnect the first ECG-electrode from the electric circuit in the first terminal unit. This further improves the electrical safety.

According to one embodiment the isolation switch arranged to connect and disconnect the first ECG-electrode from the electric circuit and its control can be implemented in a way owing to which the device is still quite small and its wearing is comfortable. Other additional advantages achieved by the invention appear in the description portion, while its characteristic features are stated in the accompanying Claims.

Figure 2A:
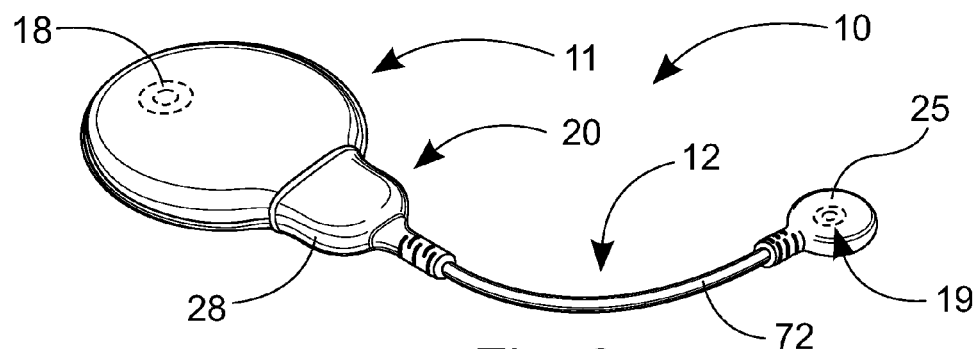
Figure 2B:
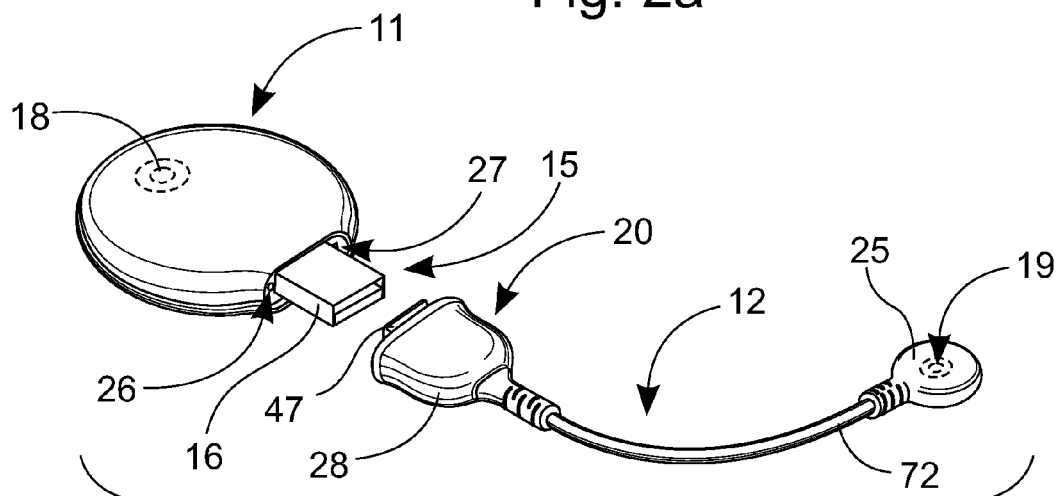
Figure 3:
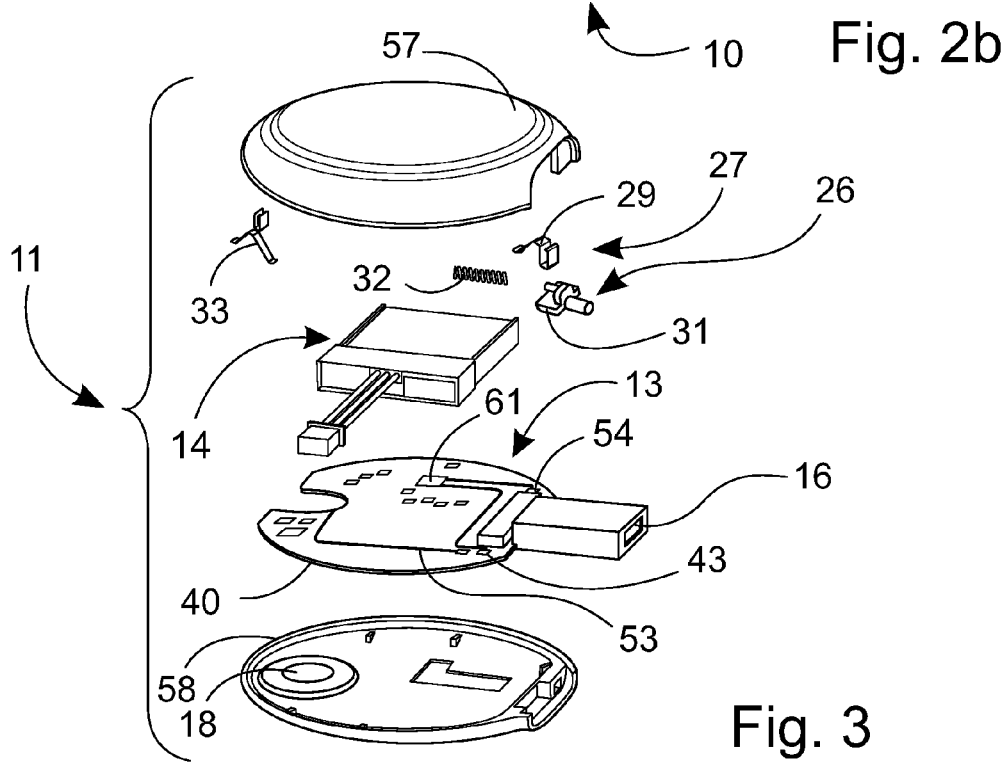
Figure 4:
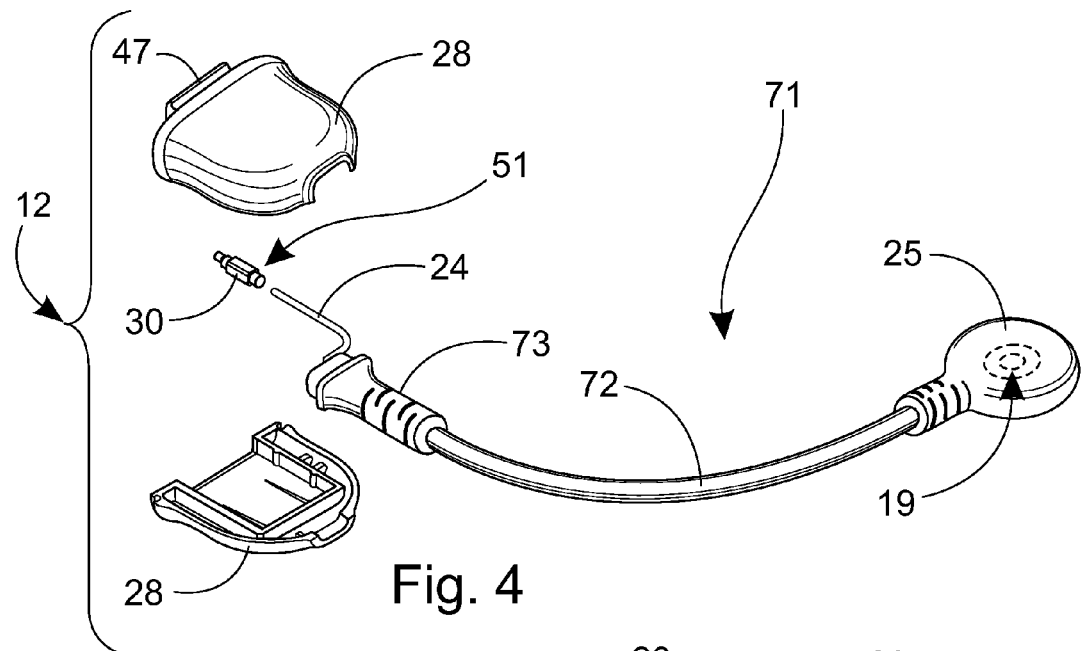
Figure 5:
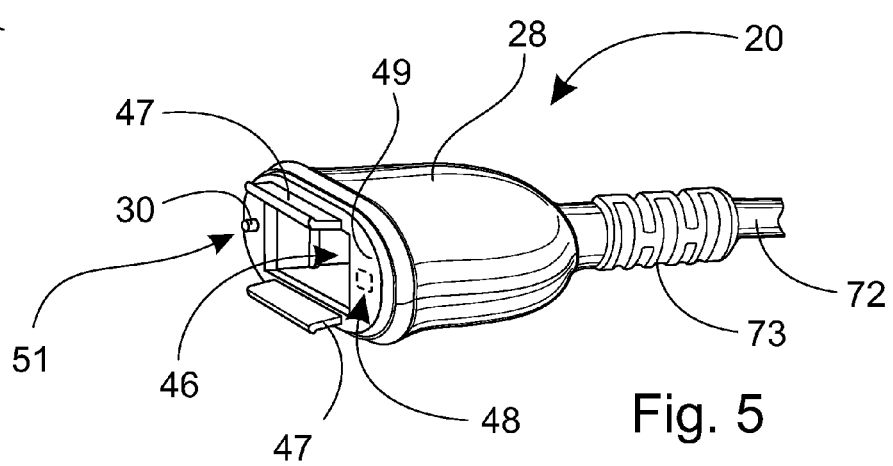
Figure 6:
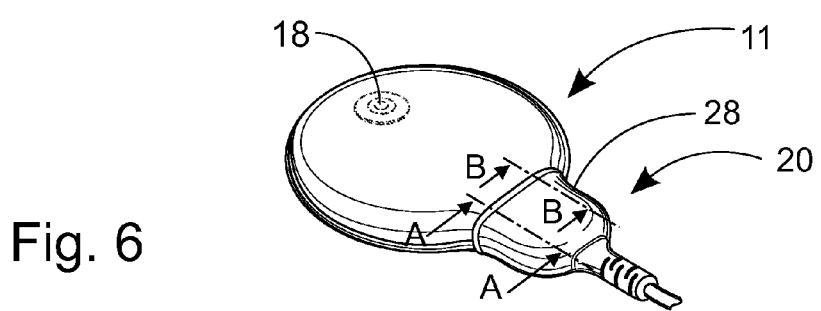
Figure 7A:
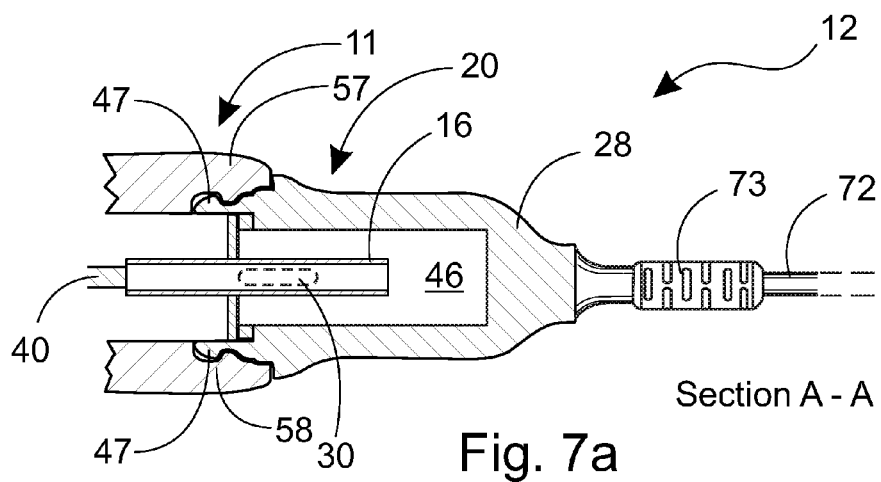
Figure 8:
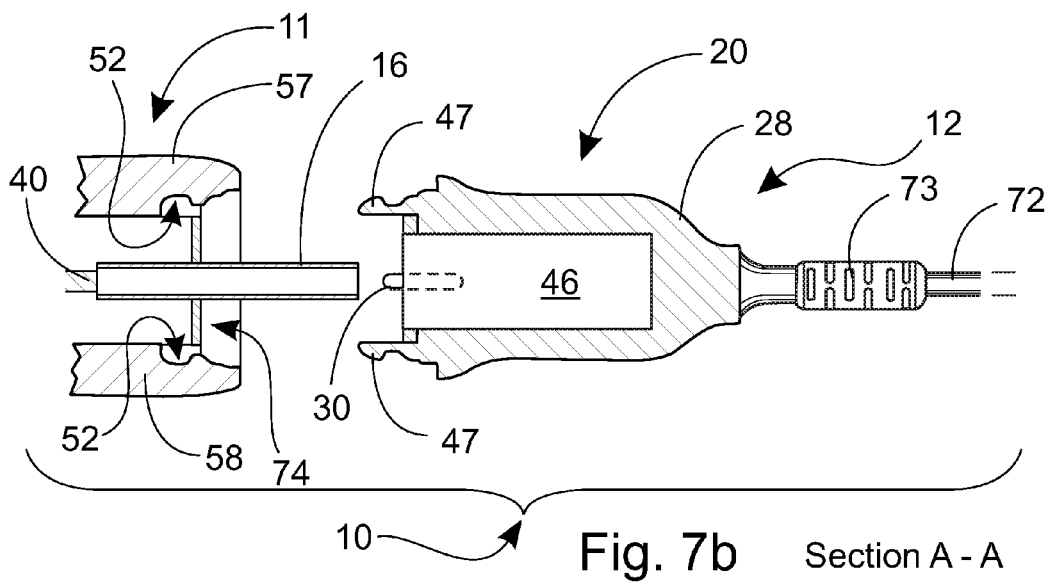
Figure 8:
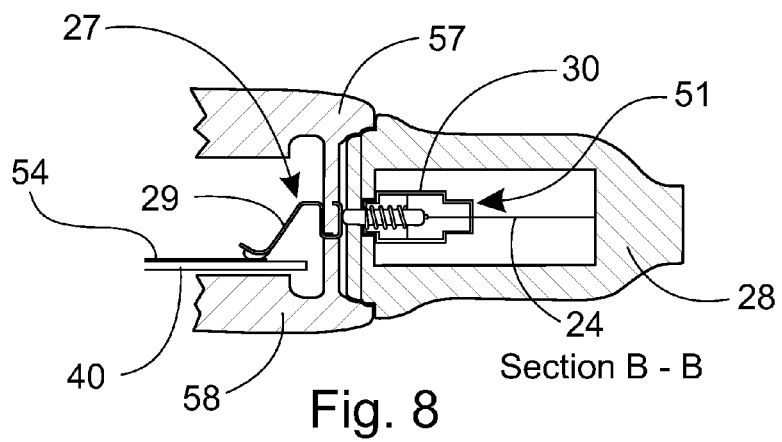
Figure 9:
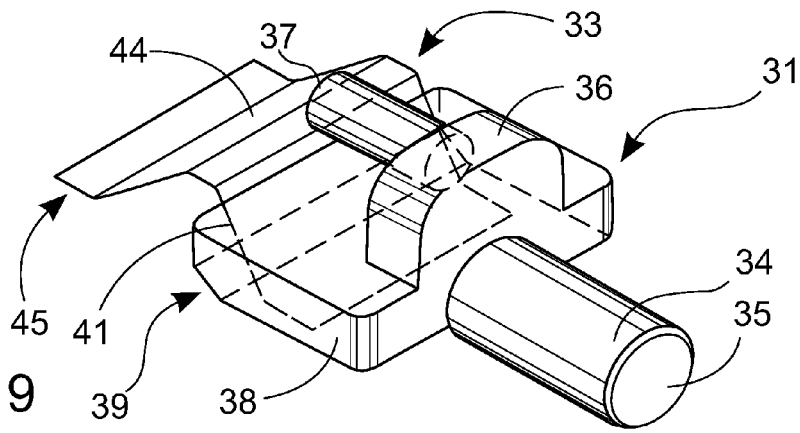
Figure 10A:
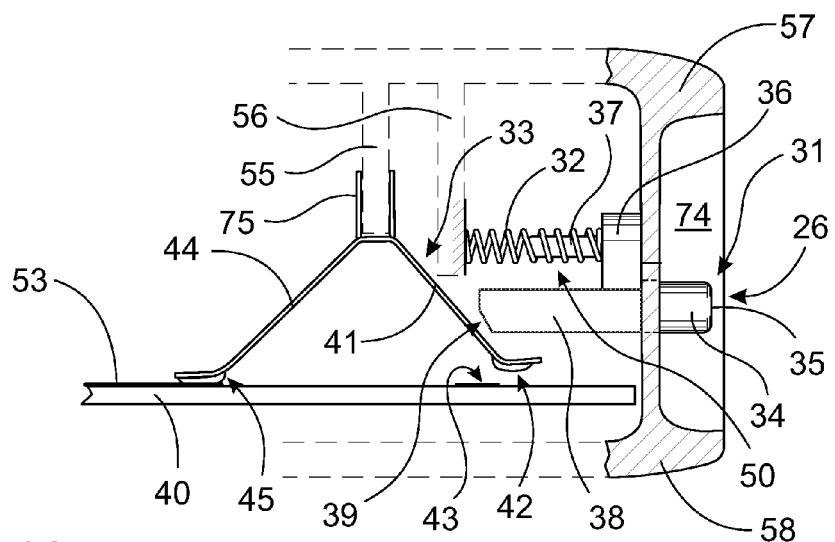
Figure 10B:
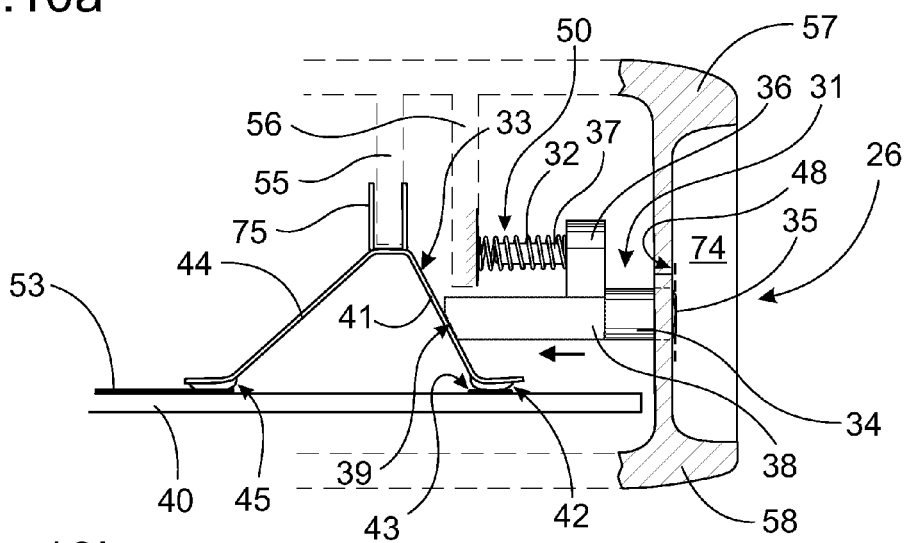
Figure 11:
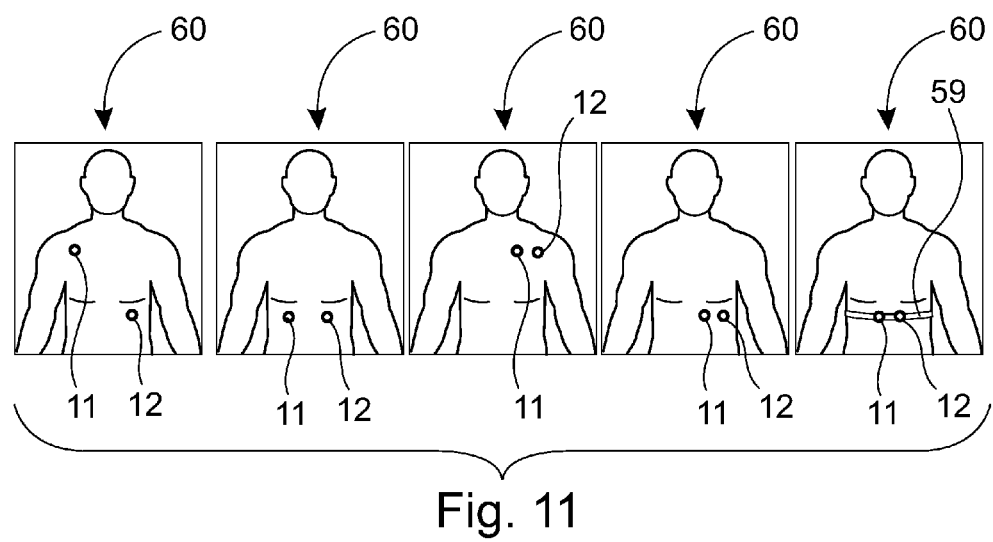
Figure 12:
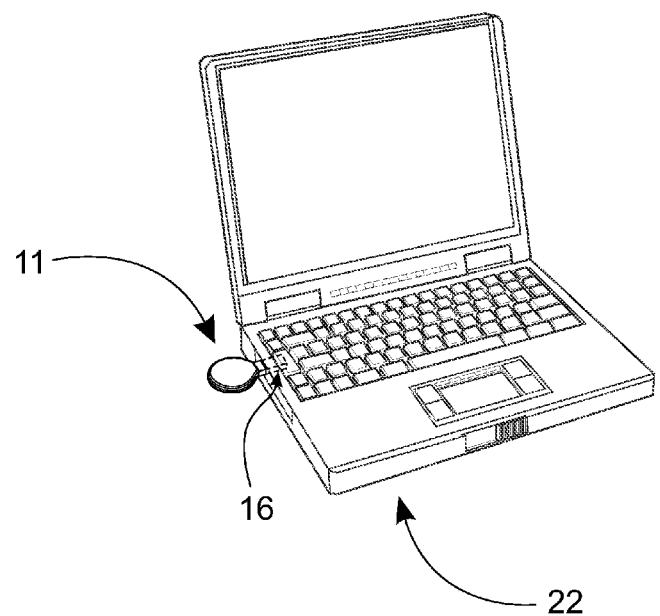
Figure 13:
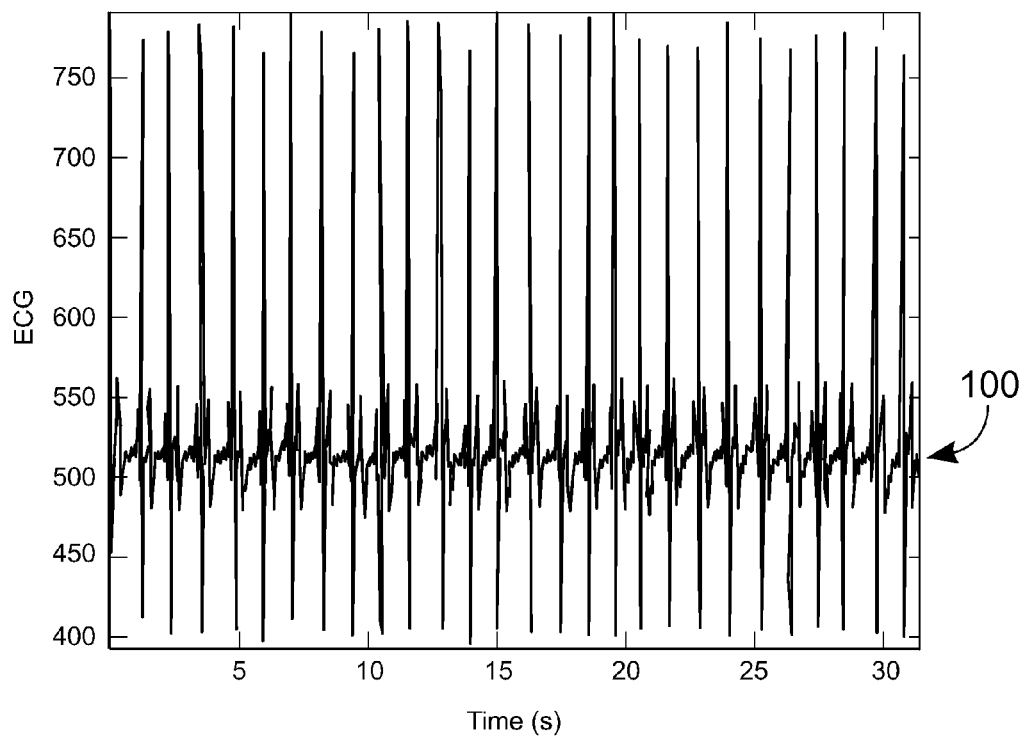
Figure 14:
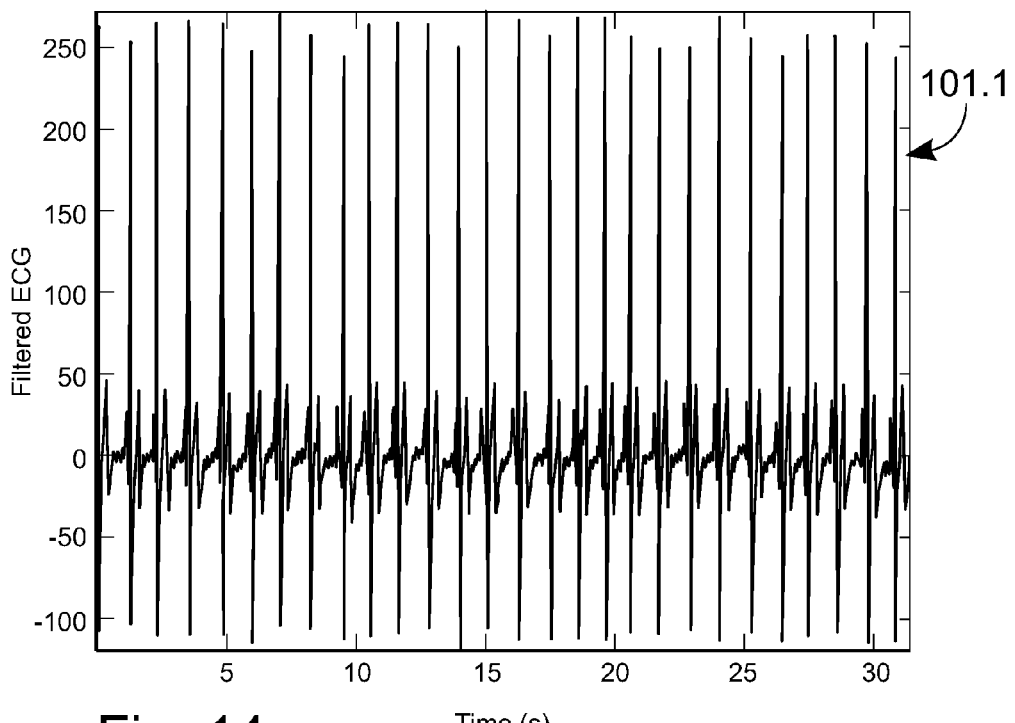
Figure 15:
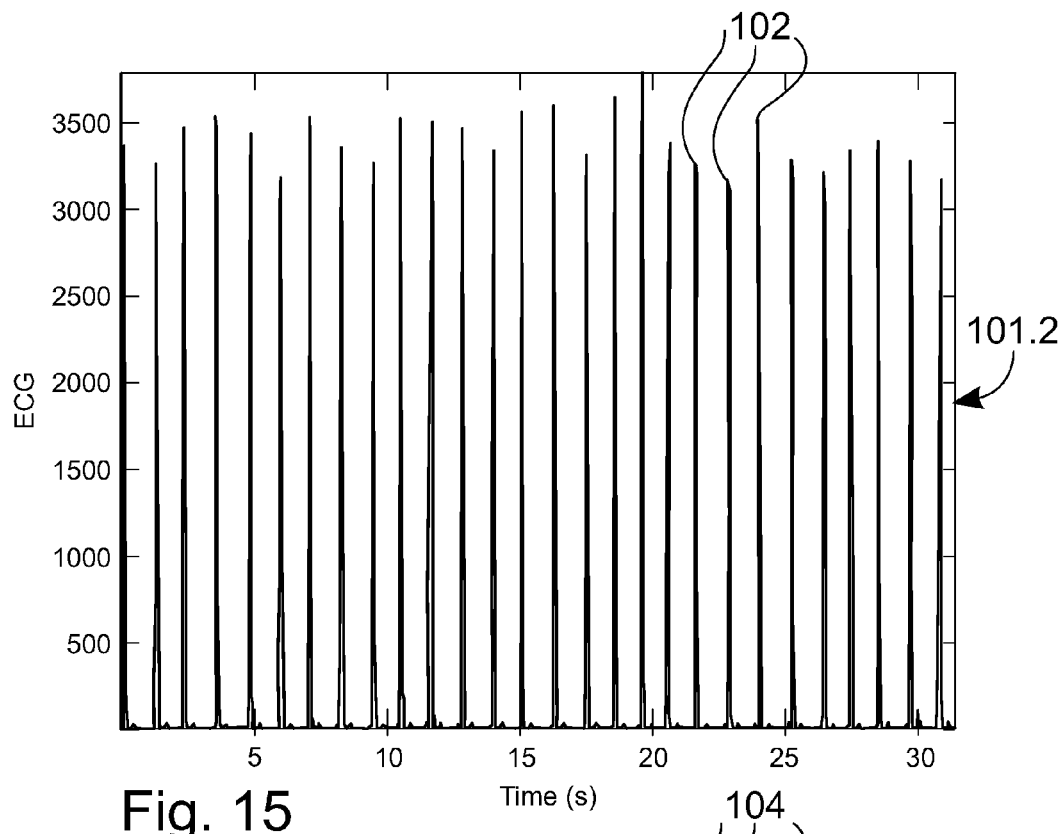
Figure 16:
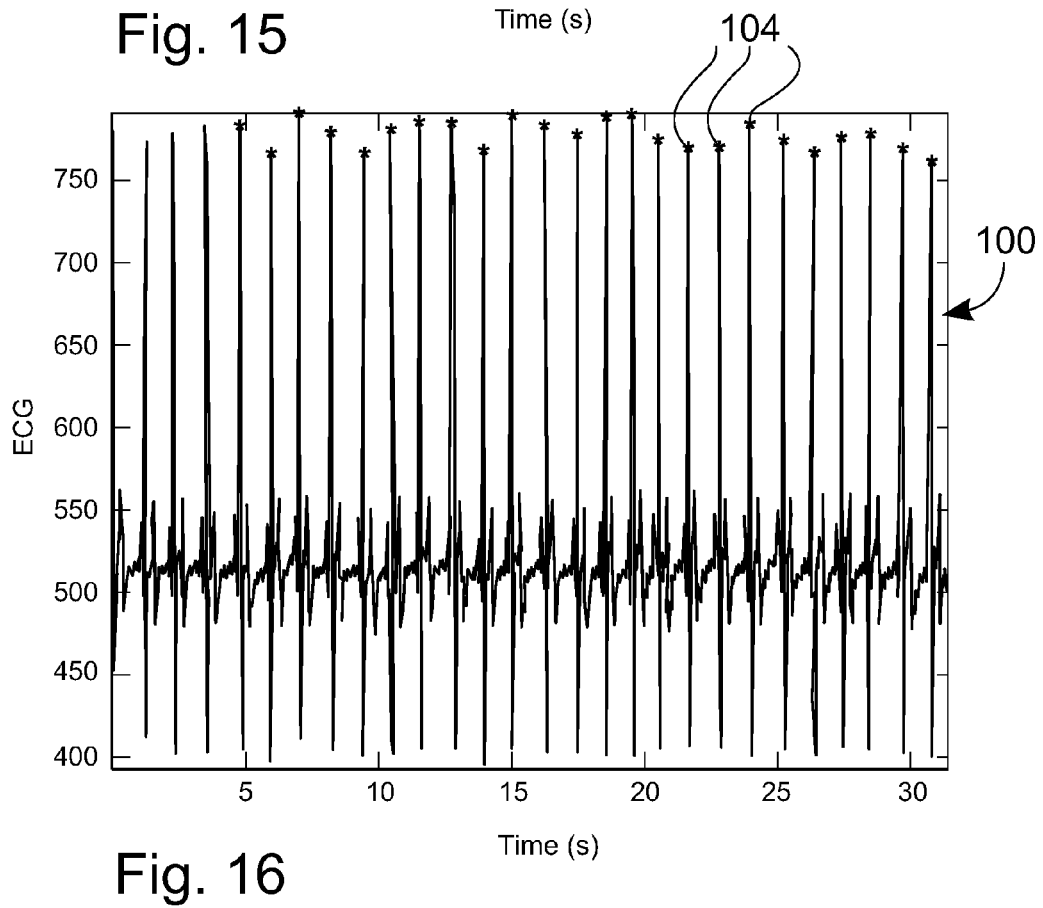
Figure 17:
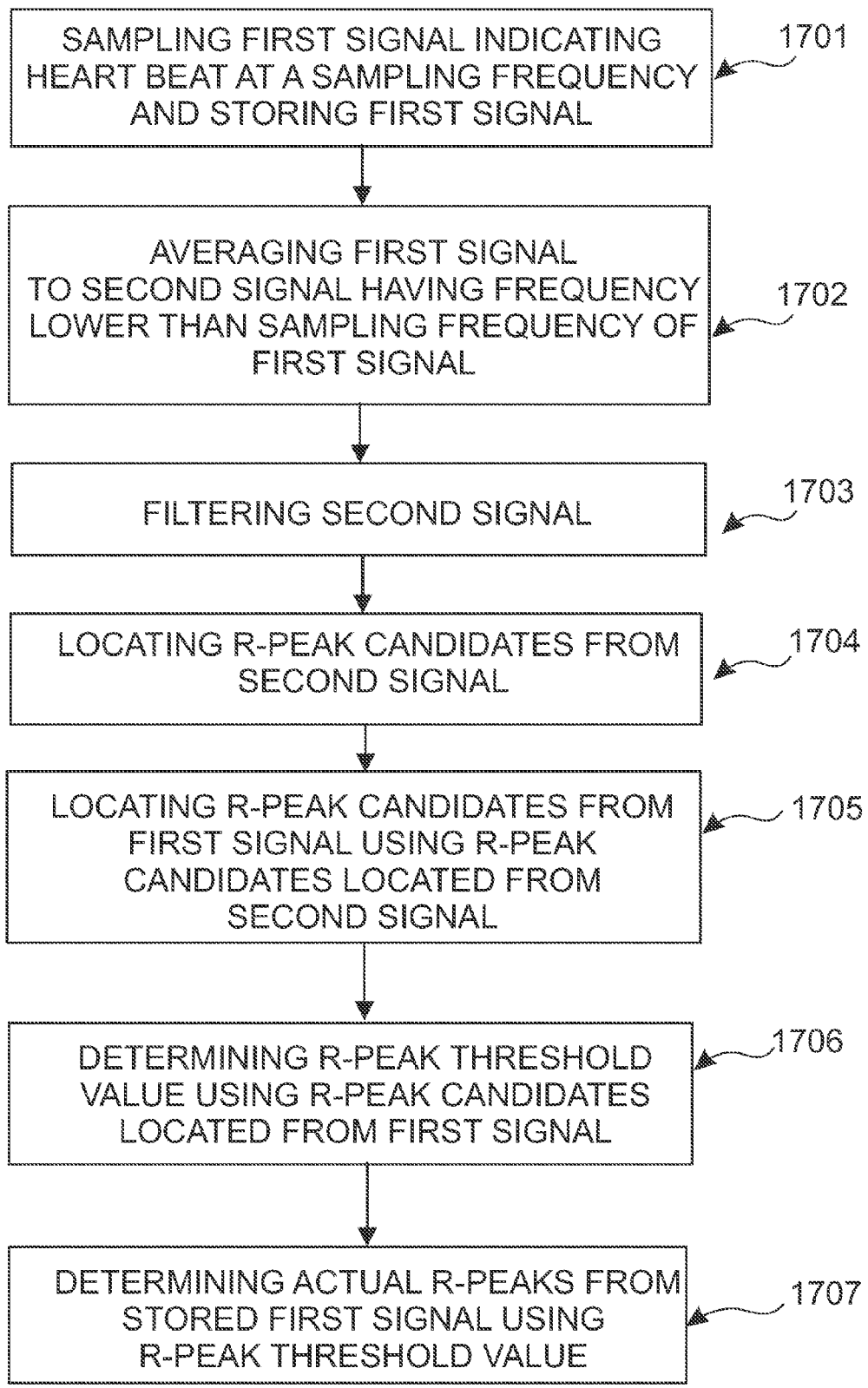

The invention, which is not restricted to the embodiments presented in the following, is described in greater detail with reference to the accompanying figures, in which FIG. 1 shows a schematic example of the device as a circuit diagram, FIG. 2a shows a schematic example of the device the terminal units as connected, FIG. 2b shows a schematic example of the device the terminal units as disconnected, FIG. 3 shows a schematic example of the first terminal unit as exploded, FIG. 4 shows a schematic example of the second terminal unit as exploded, FIG. 5 shows more detailed example of the connector assembly of the second terminal unit, FIG. 6 shows a schematic example of the cross-section points of the device, FIG. 7a shows the cross-sections of the first and second contact assemblies connected together, FIG. 7b shows the cross-sections of the first and second contact assemblies as disconnected, FIG. 8 shows the ECG-contacts between the first and second terminal unit, FIG. 9 shows an example of the switching mechanism in the first terminal unit, FIG. 10a shows the switching mechanism as disconnected, FIG. 10b shows the switching mechanism as connected, FIG. 11 shows examples of the placing the device to the body, FIG. 12 shows an example of the device when exporting data to the external device, FIG. 13 shows an example of the original 1000 Hz raw ECG-signal, FIG. 14 shows an example of the filtered ECG-signal, FIG. 15 shows an example of the filtered ECG-signal, FIG. 16 shows an example of the original 1000 Hz ECG signal with detected R-peaks marked with asterix and FIG. 17 shows an example of method as a flow chart.

FIG. 1 shows a schematic example of the main parts of the device 10 as a circuit diagram. The device 10 is meant for physiological measurement, for example. As an example of the physiological measurement is the heart rate measurement. According to one embodiment the device 10 may act as a data logger which measures human heart rate as R-R intervals. In addition, the device 10 may also measure 3D movement.

The device 10 includes an electric circuit 13 having electric components 20, 21, 61-70 coupled together implementing the functions of the device 10. The components may include, for example, signal processing means 20, 61 assembled in the electric circuit 13. These may include at least one processor unit forming a main logic 20, for example, a PIC micro-controller, an analog front end with a pre-amplifier 61 for ECG-signal and coupled to the processor 20 and power circuit 62 for energy management. Energy management module 62 may control operating voltages and battery charging, for example. Of course, the skilled person appreciates that other components may also be possible in the category of the signal processing means.

The device 10 may act as a data logger. In that case the device 10 includes also data logger means 20, 21, 67 assembled in the electric circuit 13 for storing the measured heart beats into heartbeat data and/or other measurement data. The data logger means may include a work memory 21 (buffer) and Serial Flash Memory Card 67, for example. Device 10 may store each measurement into a single file in the memory 67. The file may include, for example, measurement start time, R-R intervals and 3D accelerometer data. Device 10 may have data storage of 128 MB, for example.

The device 10 may be connected to the external device 22 after which the data stored to the memory 67 may be exported to that (FIG. 12). On the other hand, the heart beat data may also be transmitted to the external device 22 (or service) in real or mainly real time. In this case the device 10 doesn't necessarily need so big memory capacity in order to store the heartbeat data. In this case the transmitting of the data may be wireless. One example of this is the transmitting of the data to the mobile phone via Bluetooth connection 66. Of course, other transmitting methods are also possible. In this wireless embodiment, the measurement can be followed in real time for example in mobile phone or computer, or the data can be send after measurement.

In addition, the device 10 includes at least two ECG-electrodes 18, 19 and a rechargeable battery 14 (FIG. 3) coupled to the electric circuit 13. The battery may also be regular i.e. non-rechargeable. The ECG-electrodes 18, 19 are for measuring heart beats. The ECG-electrodes 18, 19 may be external and connected to the analog front end 61 which changes the analog signal to digital format and sends that to the main processor unit 20.

The device 10 includes also a connector assembly 15 (FIGS. 2*b* and 3). Connector assembly 15 includes function contacts 16 for communication with an external device 22 (FIG. 12) and/or charging the battery 14. Function contacts 16 and also the electronics 63 associated to those are for interfacing the device 10 to a PC 22, to a mobile phone and/or to a recharging adapter of the device battery 14, for example.

Function contacts include an I/O connector 16 (for example USB) coupled to the electric circuit 13 and being detachably connectable to the external device 22, for example, for exporting heartbeat data and/or a connector 16 for recharging the battery 14. The contacts 16 enable direct connection between the 10 device and PC 22 as well as device 10 charging. No separate charging cable, etc. is not necessarily required. The function contacts 16 may also allow the device 10 to be attached to a chest band wherein the chest band serves ECG-electrodes.

The I/O connector may be, for example, full speed (12 Mbit/s) male USB connector 16 which enables it to be plugged into PC USB port directly. The port may be used for PC communication, recharging the device battery 14 and/or connecting the device 10 to the other electrode (to a chest band, for example).

The battery 14 may last for 5 days measurement when R-R recording has 500 Hz sampling frequency when fully charged. The battery 14 may last for 3 days measurement when R-R recording has 1000 Hz sampling frequency when fully charged. Battery 14 can be charged with standard power grid USB hub recharger, for example. Battery 14 may be charged also when connected to PC USB port. When device battery 14 is fully charged, the battery 14 may last for 3-day measurement (500 Hz) after 3 weeks of storing.

In addition, the device 10 may also have optionally an accelerator sensor 65 (3D accelerometer) by means of which the device 10 measures movements of the user wearing the device 10. The accelerometer 65 may have sampling frequency options 5-100 Hz, 10-bit resolution and G-scale 2G, 4G or 8G. The sampling frequency and G-scale can be set in device options. The accelerometer data may be packed to smaller size, for example 50%.

Device API may communicate with external device 22 using HID interface, for example. Device 10 may not need a locally installed device driver and it can be controlled using a browser plug-in in web application. Also the device 10 could be shown as a memory stick in PC 22 (in addition to HID, for example).

The device 10 may also include the LEDs 68-70 or corresponding indication means for indicating the state of the device 10 and/or the measurement. Device 10 may have three LEDs 68-70 in front or side of the casing of the first terminal unit 11. Green LED 69 may be used to indicate successful functionality during measurement, recharging and PC connection. Amber LED 70 may be used to indicate something to be notified, such as alarm limit reach. Red LED 68 may be used to indicate failure situations during measurement.

During the measurement green LED 69 may blink in rhythm of heart rate. Device 10 is then measuring and storing R-R intervals. When green and amber LED 69, 70 blink in rhythm of heart rate the device 10 is measuring and storing R-R intervals and battery voltage is below alarm limit and/or free memory level is below alarm limit. When red LED 68 blinks in rhythm of heart rate the device 10 has recognized R-R interval signal but battery voltage is too low for measurement. When red LED 68 is on the device 10 has recognized R-R interval signal but memory is full.

During USB Connection amber LED 70 is blinking once per second device 10 is charging. When amber LED 70 is on device 10 is fully charged. When green LED 69 is on device 10 is ready to communicate with PC 22. When the device 10 is connected to power grid adapter, green LED 69 is off. When green LED 69 is blinking fast given command from PC 22 is processed. This kind of functionality (especially the LED functionality) of the device 10 is extremely easy and intuitive for the user of the device 10.

In FIG. 1 VDD is positive supply voltage of the digital parts of the circuit 13 i.e. supply voltage for processor 20, memory 21, 67 and accelometer 65. VANA is positive supply voltage for analog parts i.e. for lead detection and supply voltage for analog amplifier 61. The measurement of R-peak will be performed by the operational amplifier having supply voltage VANA. VBAT is battery voltage, which comes from battery 14. VDD and VANA are regulated supply voltages from Vbat by energy management circuit 62. Vbus is USB-interface power supply voltage (+5V). Vbus is used for charging device battery 14 etc. Device 10 detects USB-device 22 when Vbus (+5 v) is noticed and activates USB-connection. D+ and D− are USB data lines which are for USB data communications.

FIGS. 2*a* and 2*b* shows a schematic example of the device 10. The device 10 includes at least two terminal units 11, 12. The terminal units 11, 12 are detachably connectable to each other. In FIG. 2*a* the terminal units 11, 12 are connected to each other. This is the measuring mode of the device 10. In FIG. 2*b* the terminal units 11, 12 are separated i.e. detached from each other. In this setup of the device 10 the measurement is not possible, like below will be described more detailed manner. In this setup the terminal unit 11 may be connected to the external device 22 and/or to the recharging of the battery 14, for examples. From the side of the terminal unit 11 is visible the function contacts 16 which enables it to be plugged into PC and/or charger, for example. In the situation of FIG. 2*a* galvanic data loading and/or device charging are not possible because the function contacts 16 for those are not visible but enclosed by the second terminal unit 12. In addition to that the device 10 is data loading and/or device charging state in FIG. 2*b* the ECG-electrodes are not in contact to each other's and the electronic circuit 13 is not connected with metal snaps 18, 19, in generally, with the ECG-electrodes.

FIG. 3 shows a schematic example of the components of the first terminal unit 11 as exploded view. First terminal unit 11 includes the electric circuit 13, an ECG-electrode 18 and connector assembly 15 (FIG. 2b) as the first connector assembly. In addition to the function contacts 16 the first connector assembly 15 includes at least one ECG-contact 27 for connecting at least one another ECG-electrode 19 of the opposite terminal unit 12 (FIG. 2b). The ECG-contact 27 may be implement by the component 29 the function of which has been described in FIG. 8 more detailed manner. In addition, the first terminal unit 11 may also have an isolation switch 26 the function of which has been described in FIGS. 10a and 10b more detailed manner. According to one embodiment the isolation switch 26 may be implement by the components 31-33.

The electric circuit 13 is now on one printed circuit board 40 (PCB). The PCB 40 has the electrical connection 43 from the isolation switch 26 and the electrical connection 54 from the ECG-contact 27 to the signal processing means 61. In addition, the PCB 40 has also the electrical connection 53 from the ECG-electrode 18 to the isolation switch 26. The components of the first terminal unit 11 are enclosed in the casing that is now formed of two covers 57, 58. Casing as assembled has openings for the first connector assembly 15, i.e. now for the USB connector 16 suitable for data transfer i.e. communication and/or charging of the battery 14 and, in addition, for the isolation switch 26 and for the first ECG-contact 27. The ECG-electrode 18 is attached to one of the covers 58 of the casing.

The ECG-electrode 18 located in the cover 58 may be a metal snap to which the external electrode attached to the body may be attached. The metal snap 18 is embedded in the cover 58 wherein the device 10 is as close to body as possible, minimize the device 10 wiggle and the detection of the acceleration signal is also reliable.

FIG. 4 shows a schematic example of the second terminal unit 12 as exploded and FIG. 5 more detailed example of the connector assembly 20 of the second terminal unit 12. The device 10 includes at least one terminal unit 12 that is opposite for the first terminal unit 11. The second terminal unit 12 is now a wire-like strip. This opposite terminal unit 12 includes another of ECG-electrodes 19 and, in addition, second connector assembly 20. Between the ECG-electrode 19 and the second connector assembly 20 is a lead 24 of the ECG-electrode 19 that is enclosed to the case 25. The cable assembly 71 of the second terminal unit 12 includes a cable 72, strain relief 73 and metal snap 19 with over molded plastic 25. Metal snap acts now as an ECG-electrode 19 with the sticker electrode to be attached to the body. Cables 72 can be of different lengths and different materials. At the same device 10 may have a number of terminal units 12 with different lengths of the cables 72. The plug 20 attached to the cable 72 can be changed or replaced without new device changing. This is considerable advantage of the device 10 formed of at least two detachably connectable parts i.e. terminal units 11, 12.

The second connector assembly 20 has a counter ECG-contact 51. The counter ECG-contact 51 is adapted to be fitted to the ECG-contact 27 of the first connector assembly 15 of the first terminal unit 11 when the terminal units 11, 12 are connected together. The lead 24 of the ECG-electrode 19 is connected to the counter ECG-contact 51. The counter ECG-contact 51 may be, for example, a pogo pin 30 enclosed mainly into the second connector assembly 20.

The casing of the second connector assembly 20 may be formed of two cover portions 28. The covers 28 as jointed an open cavity 46 is formed which embeds at least part of the function contacts 16 of the first terminal unit 11 when the terminal units 11, 12 are connected together. In addition, the covers 28 form also the frontal surface 49 around the opening of the cavity 46. The contact portion of the pogo pin 30 extrudes from the frontal surface 49 at one side that is next to the opening of the cavity 46. At the opposite side relative to the opening of the cavity 46 the frontal surface 49 forms a butt member 48 of the isolation switch 26, which butt member 48 the second connector assembly 20 also includes in this embodiment.

The terminal units 11, 12 include shape locking formations 47, 52 for connecting them together detachably. One possible way to implement this is to arrange to the second connector assembly 20 protruding shelf members 47 being horizontally on upper and lower edges of the frontal surface 49 next to the opening of the cavity 46. These members 47 may be flexible and fit to the indentations 52 being in the hollow recess 74 of the first terminal unit 11 (FIG. 7b) and form the shape locking between the terminal units 11, 12. The top cover and the bottom cover 28 of the second connector assembly 20 of the second terminal unit 12 may be different shaped, in which case the plug's 20 wrong attachment to the terminal unit 11 is impossible. The shape locking is simple and also reliable. It enables easy connection of the units 11, 12 and also detachment.

FIG. 6 discloses the terminal units 11, 2 as connected and the cross-section lines A-A and B-B disclosed further. FIG. 7a shows the cross-sections A-A of the terminal units 11, 12 as connected and FIG. 7b as disconnected. Terminal units 11, as connected together are arranged to connect the ECG-electrode 19 of each opposite terminal unit 12 to the electric circuit 13 in the first terminal unit 11.

FIG. 8 shows the examples of the ECG-contacts 27, 51 between the first and second terminal unit 11, 12 in more detailed. In the present embodiment the pogo pin 30 acting as a counter ECG-contact 51 of the second connector assembly 20 is fitted against the ECG-contact 27 of the first connector assembly 15 when the units 11, 12 are connected together (FIGS. 2a and 7a). The counter ECG-contact 51 may be, for example, a pogo pin 30 enclosed mainly into the second connector assembly 20. The electrically conductive pin portion protrudes out from the connector assembly 20 by a spring force. The frontal surface 49 of the connector assembly 20 has an opening for this pin.

The design of the first ECG-contact 27 may be a bended sheet metal piece forming a flat spring 29. The flat spring 29 is supported to the structures of the casing 57, 58 of the first terminal unit 11. At one end the contact portion of the flat spring 29 is visible from the casing of the first terminal unit 11 against which the pogo pin 30 of the second connector assembly 20 of the second terminal unit 12 sets when the terminal units 11, 12 are connected together. Pogo pin 30 connects the cable 24 of the ECG-electrode 19 to the electronics 13 through this contact spring 29. From the opposite end of the flat spring 29 it is contacted to a lead 54 being in the PCB 40. The lead 54 goes to the pre-amplifier 61 (FIGS. 1 and 3). The contact between the first ECG-contact 27 and the second ECG-contact 51 is flexible. In addition to flat spring the pogo pin 30 also includes a spring member causing spring force. This makes the contact very reliable.

Like FIG. 7a discloses when the terminal units 11, 12 are connected together the function contacts 16 are not visible. In this setup the function contacts 16 are in the cavity 46 of the second connector assembly 20. The cavity 46 is arranged to embed at least part of the function contacts 16 when the terminal units 11, 12 are connected together. This prevents to connect the device 10 to the external device 22 and/or charging when the ECG-electrode 19 of the second terminal unit 12 is connected to the electric circuit 13, for example. This kind of embedding of the function contacts 16 is easy to arrange. In addition, hiding of the function contacts 16 makes the design of the device 10 smooth when that is in the measurement mode and worn by the user.

Like FIG. 7b discloses the terminal units 11, 12 as separated are arranged to enable the use of the function contacts 16 of the first connector assembly 15. In this separated mode the first terminal unit 11 is connectable to the external device 22 and/or to enable charging of the battery 14 through the function contacts 16 (USB pins) which are now in view. In addition, in the setup of FIG. 7b the ECG-electrode 19 is not coupled to the electric circuit 13 because the units 11, 12 are separated and due to this reason there is no connection between the ECG-contact 27 of the first terminal unit 11 and the counter ECG-contact (pogo pin 30) of the second terminal unit 12.

In addition, according to one embodiment the terminal units 11, 12 as separated may also be arranged to disconnect the first ECG-electrode 18 from the electric circuit 13 in the first terminal unit 11. According to this the both ECG-electrodes 18, 19 may be physically switched off when the two parts 11, 12 of the device 10 are separated. For this purpose the first connector assembly 15 may include an isolation switch 26 arranged to connect and disconnect the first ECG-electrode 18 from the electric circuit 13. The location of the isolation switch 26 in the first terminal unit 11 has been disclosed in FIG. 2b.

The isolation switch 26 may include according to one embodiment a switching mechanism 31, 33 and release mechanism 50 of the switching mechanism 31, 33. FIG. 9 discloses an example of the switching mechanism 31, 33 arranged to the first terminal unit 11. The switching mechanism includes now an operating member 31 and a contact member 33. Operating member 31 is a button arranged to connect the contact member 33 to the electric circuit 13. The operating member 31 is a shaped piece having operating lug 34 with an end surface 35. The piece 31 have a support pin 37 for the release mechanism 50 and push member 38 with pushing surface 39.

The contact member 33 is now a bended sheet metal piece having two legs 41, 44 and forming an electrode spring. One leg 41 will be placed against the pushing surface 39 of the button 31 when the switching mechanism is assembled. The other leg 44 has a contact 45 at its end. The contact 45 will be contacted to the electric lead 53 on the PCB 40 when the switching mechanism is assembled.

Correspondingly, the second connector assembly 20 includes butt member 48 of the isolation switch 26. An example of the butt member 48 has been disclosed in FIG. 5. When the terminal units 11, 12 are connected together the butt member 48 is arranged to effect to the isolation switch 26 and especially to the button 31.

FIG. 10a shows the switching mechanism 31, 22 as disconnected and FIG. 10b shows the switching mechanism 31, 33 as connected. According to one embodiment the release mechanism 50 may include a coil spring member 32 connected to the operating member 31. Now the spring member 32 is fitted to the support pin 37 in the operating member 31. At the opposite end the spring member 32 is against the support structure 56 formed to the upper cover 57 of the casing. The contact member 33 may have attachment groove 75 on the upper fold point between the legs 41, 44. The cover 57 of the casing may have a structure 55 which can be fitted to the groove 75 to secure the contact member 33 in its position in the assembly.

In FIG. 10a the spring member 32 presses the operating member 31 against the inner side of the cover structure 57, 58 of the unit 11. The lug 34 is protruded from the casing to the recess space 74 arranged to the first connector assembly 15 for the second connector assembly 20. The recess assembly 74 is formed by the flanges being in the covers 57, 58. Owing to this the operating member 31 does not press the contact member 33 of the isolation switch 26 so the leg 41 of the contact member 33 is disconnected from the lead 43 in the PCB 40. Thus, the ECG-electrode 18 in the first terminal unit 11 is not connected to the electric circuit 13 because the circuit is disconnected. When the contact button 31 is not pressed electronic circuit 13 is not connected with the ECG-electrode 18. So when the device 10 is connected to a computer 22 or to a charger, voltage is not connected to the ECG-electrode 18 and the current may not enter the human body via electrodes (mechanical power protection).

In FIG. 10b the terminal units 11, 12 are connected together. Owing to this the device 10 is in measuring mode and the isolation switch 26 connects the ECG-electrode 18 to the electric circuit 13 in the first terminal unit 11. In that case the second connector assembly 20 of the terminal unit 12 is obtruded to the hollow recess 74 in the first terminal unit 11. The butt member 48 in the frontal surface 49 of the second connector assembly 20 presses the operating member 31 of the switching mechanism 26. Owing to this the operating member 31 moves towards the leg 41 of the contact member 33 and the pushing surface 39 of the operating member 31 pushes the leg 41 of the contact member 33. The contact 42 in the end of the leg 41 reaches the lead 43 on the PCB 40 and the circuit is connected. This lead 43 goes to the analog front end 61 on the PCB 40. Because the opposite leg 44 of the contact member 33 is fixedly contacted to the lead 53 of the ECG-electrode 18 that is now connected to the electric circuit 13. In other words, the electrode spring acting as a contact member 33 connects the electrode 18 of the first terminal unit 11 to the electronics 13 through switch 26 which is activated when the terminal units 11, 12 are connected together. Measurement of the voltage between two, for example, sticker electrodes connected to the ECG-electrode 18, 19 is possible when the terminal units 11, 12 are connected together and the device 10 is in the measuring mode (FIG. 2a).

When the terminal unit 12 is again detached from the first terminal unit 11 the coil spring 32 restore the operating member 31 back to the setup presented in FIG. 10a. In other words, the coil spring 32 is used to release the switch 26 when second terminal unit 12 is not connected to the first terminal unit 11. Owing to this the push member 38 doesn't push anymore the leg 41 of the contact member 33 and the contact between the leg 41 and the lead 43 is lost due to the return motion caused by the spring effect in the contact member 33. Then the ECG-electrode 18 is no more in electrical contact with the electric circuit 13 or USB-connector 16. In other words, disconnecting the terminal units 11, 12 disconnects both electrodes 18, 19 from the electronics 13. These components 29, 31-33 arrange isolation to the ECG-electrodes 18, 19 and the connection to the USB (or a respective connector) is disconnected.

The isolation switch 26 and also the ECG-contact 27 mechanism between the units 11, 12 are very compact and durable constructions fitted to the limited space being inside the device 10. Owing to these the size of the device 10 is reasonable. The thickness of the device 10 may be, for example, 9 mm and the weight of the device 10 may be, for example, 20 grams. Owing to this the device 10 is very unnoticeable and its wearing convenience is excellent. In addition, the mechanisms 26, 27 are also very reliably. Because the device 10 case is waterproof and it can be used being 4096 ms. In the table below is shown the interrupt during measurement. The integrity is checked with formula:

<Measurement end time>−<Measurement start time>=Sum(R-R intervals)

|  | R-R1 | R-R2 | R-R3 | R-R4 | R-R5 | R-R6 | R-R7 | R-R8 | R-R9 | R-R10 |
| --- | --- | --- | --- | --- | --- | --- | --- | --- | --- | --- |
| ms | 520 | 530 | 533 | 527 | 4096 | 4096 | 3895 | 765 | 767 | 812 |
| 2 byte | 208 | 212 | 215 | 020F | FFFF | FFFF | 86A0 | 02FD | 02FF | 032C | while swimming and in shower the repairing of the mechanisms 26, 27 is not possible. Thus, the device 10 does not need to be able to be disassembled. In addition, the due to the mechanisms 26, 27 the device 10 withstands dropping to a hard floor tile from 1.5 meter height without breaking. In generally, the durability properties are very important for the devices used in fast activities.

The device may also include three or even more parts. In that embodiment the electrode connection is lost and the electrical circuit 13 is disconnected when the third part of the device is removed manually from the device 10.

FIG. 11 shows examples of the placing the device 10 to the body 60. The device 10 may be attached to the skin in different parts of the body 60. The device 10 is attached to the body 60, for example, with standard disposable sticker electrodes with stud connector or to the chest band 59 with connector. The sticker electrodes connects to the ECG-electrodes 18, 19 of the device 10 forming effectively the ECG-electrodes. The measurement starts automatically when the device 10 is attached to the body 60 and the device 10 detects an ECG signal. The device 10 stores the data to internal data storage for further data upload to PC 22 or web service. The measurement may take place 24 hours a day for up to 7 days.

Instead of the disposable sticker electrodes the whole ECG-electrode functionality may be in the device 10 itself. In that case the ECG-electrodes 18, 19 are so called dry electrodes in the heart-rate belt, for example. In other words, the ECG-electrodes 18, 19 may be understood as ECG-electrode terminals having electrode functionality integrated to the device 10 or suitable for connecting to the external sticker electrodes (or corresponding), for example.

The signal is taken by A/D converter 61 in frequency of 500 Hz or 1000 Hz. The frequency can be set in device settings. Resolution may be 10-bits. Device 10 has an option for recording the ECG data (instead of R-R data). In ECG mode the device 10 bypasses the R-peak recognition and stores the ECG signal to the measurement file instead of the R-R data. The ECG recording is alternative to the R-R recording in device settings.

Device 10 may work automatically without any buttons (except the reset button). Device 10 may have the following states:
a. "ON" when R-R interval signal is recognized.
b. "SLEEP" when R-R interval signal has not been received within a time limit. The time limit can be modified in device settings. Moving to state "SLEEP" ends measurement.
c. "CHARGING" when USB cable is plugged in either to PC or power grid adapter.
d. "COMMUNICATING" when communication is triggered by PC or by radio transmitter.

Device 10 may keep up the R-R data integrity. During interrupts in measurement the interrupt time is attached to the R-R interval series in milliseconds, the highest value The example above has proper signal for R-R intervals 1, 2, 3 and 4. Then signal is lost for 12087 milliseconds (stored as beats 5, 6 and 7). The last three beats are correct intervals. Total time for this example measurement is 16541 milliseconds.

FIG. 12 shows an example of the device 10 when exporting data to the external device 22 which is a laptop computer in this case. Device 10 can be controlled and read in Windows, Mac OS and Linux and in those Android and Windows phones that can operate as master for devices. Due to the recess assembly 74 the operating lug 34 is always safely in the recess 74 of the first terminal unit 11 and it will not be accidentally pressed when the device 10 is connected to the external device 22 and/or charging (FIGS. 10*a* and 10*b*).

For example, in the device 10 according to the invention it is possible to perform processing method of ECG-signal, or in general, a signal indicating a heartbeat, for the R-peak detection, for example, or in general, a heartbeat. FIG. 17 shows an example of method as a flow chart. FIG. 13 shows an example of the original raw ECG-signal 100 sampled at 1000 Hz frequency, for example. The algorithm may detect R-peaks of the 1000 Hz sampled ECG-signal 100 which is averaged and filtered to 250 Hz. The algorithm may be implemented for real-time analysis working with online ECG-device 10, for example. According to one embodiment in the case of ECG-processing the method may include the next steps, for example.

In step 1701 the first signal indicating a heartbeat 100 is sampled at a sampling frequency, for example, 1000 Hz. The first signal 100 is so called raw signal and it is stored to the memory 21 of the device 10. Storing of the first signal 100 may be done to the buffer memory 21 within a chosen period.

In step 1702 may be performed a downsampling of the first signal 100 to a second signal. The second signal has frequency lower than the sampling frequency of the first signal 100. According to one embodiment the downsampling may be, for example, averaging of the first signal 100 or also any other method in order to reduce sampling rate (time resolution) of the signal (for example, spaced sampling of the sampled first signal 100).

In the present embodiment the raw ECG-signal 100 having sampling frequency 1000 Hz is averaged to a second signal having reduced frequency of 250 Hz. In other words, a sampled ECG-signal 100 is averaged to a signal having frequency lower than a frequency of the sampled ECG-signal 100.

According to one embodiment averaging of the 1000 Hz signal 100 to 250 Hz signal may be done by simply calculating average of the last four ECG samples, for example. Averaging may be done, for example, every time a total of four new samples is found, i.e., only last four values needs to be stored.

In step 1703 the averaged, or in general, downsampled ECG-signal i.e. the second signal may be filtered. Filtering step may include one or more filtering procedures. Filtering performed for the signal having reduced frequency relative to the sampling frequency saves power. According to one example filtering may contain, for example, removing of the moving average of the 250 Hz ECG-signal. Moving average window may be, for example, 5 seconds, i.e., 1250 samples long. FIG. 14 shows the 250 Hz filtered ECG-signal 101.1 after removing of the moving average.

In addition, the filtering step 1703 may also contain one or more low pass or high pass filters to remove frequency-components out of interest, for example. In addition, the filtering step 1703 may also contain squaring and averaging of the 250 Hz second signal, for example. Averaging window may be, for example, 60 ms long (15 samples). FIG. 15 shows the 250 Hz filtered ECG-signal 101.2 after the filtering stages 1703 presented in this embodiment.

In step 1704 R-peak candidates 102, or in general, heartbeat candidates, are located from the filtered ECG-signal 101.2 using a predetermined criteria. According to one embodiment this may be done window-basis, for example, for each 250 ms window of the filtered ECG-signal 101.2. 250 ms is considered to be the shortest physiologically possible RR-interval.

According to one embodiment the determination of the predetermined criteria for locating the R-peak candidates may include the next steps. After R-peak candidate 102 is located from the filtered ECG-signal 101.2 the accurate location of the R-peak candidate 102 may be located from 1000 Hz sampled original ECG-signal 100 (in step 1705) using the R-peak candidates 102 located from the filtered ECG-signal 101.2. This may be done by detecting the local maximum nearby the detected location from 1000 Hz sampled original ECG signal 100. This saves power.

In step 1706 may be determined a R-peak threshold value, or in general, a heartbeat threshold value, using the R-peak candidates 102 located from the raw ECG-signal 100. In this twelve (12) last R-peak candidates may be saved to the memory 21 to calculate current R-peak threshold. Thus, R-peak threshold is not constant but dynamic adjusting itself to dynamic changes in ECG-signal. Owing to the dynamic adjusting the method scales to different R-peak amplitudes which may vary between the persons to be measured. Only those R-peak candidates that exceed the threshold are finally accepted as R-peaks. The storage size may be defined by 250 ms×12=3000 ms which may be considered as longest physiologically possible RR-interval. According to one example the threshold may be defined as maximal R-peak candidate in storage divided by seven (7). Further-more, the threshold is at least one (1).

FIG. 16 shows the original 1000 Hz ECG signal 100 with detected R-peaks marked with asterix. On the basis of the R-peak threshold value are determined the R-peaks 104 in step 1707. In generally, R-peaks 104 are determined from the stored first signal 100 on the basis of the R-peak candidates located from the second i.e. filtered ECG-signal. In this the R-peak candidates of the first ECG-signal 100 that exceed the threshold are accepted as actual R-peaks. Each R-peak 104 is accurately located and are local maxims. The first four R-peaks are not located as the algorithm may require short starting time to adjust for the signal.

The algorithm processes the heaviest calculus with 250 Hz signal saving CPU time and reducing power usage of the microcontroller 20. Locating the exact R-peak location from the original 1000 Hz signal 100 preserves the 1000 Hz accuracy of the algorithm minimizing the R-peak location error.

In the pilot stage tests the algorithm was empirically optimized by analyzing over 6000 minutes of 1000 Hz real-life ECG-data containing rest, sleep, sports and daily activities. The optimal algorithm and parameters were achieved by minimizing the overall amount of RR-interval artifacts in the data with given parameter set.

The algorithm presented above may be applied not only in the devices 10 according to the invention but also in several different kind of devices in which ECG-signal processing have been performed. Some non-limiting examples of these devices are ECG devices in general, heart rate belts and/or PPG (photoplethysmography) devices. In PPG-devices the peak of the wave (or corresponding) is located instead of the R-peak. In other words, the terms "R-peak", "R-peak candidates" and "R-peak threshold value" should be understood very widely in this connection (generally heartbeat).

The invention concerns also the device 10 implementing at least one or more method steps presented above and also the computer program comprising one or more sequences of one or more instructions which, when executed by one or more processors 20, cause a device 10 to at least perform the method.

The device 10 may primarily be used by health care employees, such as doctors, nurses and physiotherapists or other professional users who will have training for the use of the device (professional users). The measurement is applied to common people (end users) who do not have any special technical skills. The professional users control the device 10 using Firstbeat or respective software.

Secondarily the device 10 may be used in sports segment. In sports the device 10 may be owned and fully used by athletes. The example of use in sports segment is night recovery analysis and secondarily it may also be used as logger during exercise. In this embodiment an additional chest band with dry electrodes may be required.

Measurement reliability has special focus and it must be very close to 100%. User invests typically 3-5 days of his time to this measurement (wears the device and fills in a journal) and failure in measurement is a huge disappointment.

It must be understood that the above description and the related figures are only intended to illustrate the present invention. The invention is thus in no way restricted to only the embodiments disclosed or stated in the Claims, but many different variations and adaptations of the invention, which are possible within the scope on the inventive idea defined in the accompanying Claims, will be obvious to one skilled in the art.

The invention claimed is:

1. A device for physiological measurement including at least two terminal units connectable to each other, comprising:
    a first terminal unit includes an electric circuit having electric components implementing functions of the device, a first ECG (electrocardiogram)-electrode connected to the said electric circuit and a first connector assembly having at least one ECG-contact for connecting at least one another ECG-electrode to the said electric circuit, the electric circuit having signal processing means assembled therein and a battery coupled to it,
    at least one opposite terminal unit including a second ECG-electrode and second connector assembly having a counter ECG-contact and adapted to be fitted to the ECG-contact of the first connector assembly, wherein at least two ECG-electrodes including the first ECG-electrode of the first terminal unit and the second ECG-electrode of at least one opposite terminal unit are to be coupled to the said electric circuit for measuring heart beats, wherein the first connector assembly includes function contacts connected to the said electric circuit for communication with an external device and/or charging the battery, wherein the first terminal unit and at least one opposite terminal unit, as connected together, are arranged to connect the ECG-electrode of each opposite terminal unit including the first ECG-electrode of the first terminal unit and the second ECG-electrode of at least one opposite terminal unit to the said electric circuit in the first terminal unit, wherein the first terminal unit and at least one opposite terminal unit, as separated, are arranged to enable the use of the function contacts of the first connector assembly connected to the said electric circuit, and to disconnect the first ECG-electrode of the first terminal unit from the said electric circuit in the first terminal unit.

2. The device according to claim 1, wherein the first connector assembly includes an isolation switch arranged to connect and disconnect the first ECG-electrode of the first terminal unit from the electric circuit, and the second connector assembly includes a butt member of the isolation switch.

3. The device according to claim 2, wherein the isolation switch includes a switching mechanism and a release mechanism of the switching mechanism, and the butt member is arranged to effect to the switching mechanism.

4. The device according to claim 3, wherein the switching mechanism includes an operating member arranged to connect a contact member to the electric circuit, and the release mechanism includes a spring member connected to the operating member.

5. The device according to claim 1, wherein the ECG-contact of the first terminal unit and the counter ECG-contact of the opposite terminal unit are flexibly connected.

6. The device according to claim 5, wherein the ECG-contact of the first terminal unit is a flat spring and the counter ECG-contact of the opposite terminal unit is a pogo pin.

7. The device according to claim 1, wherein the second connector assembly includes a cavity arranged to embed at least part of the function contacts when the terminal units are connected.

8. The device according to claim 1, wherein the terminal units include shape locking formations for connecting them together detachably.

9. The device according to claim 1, wherein the device is arranged to act as a logger and includes a data logger assembled in the electric circuit for storing the measured heart beats into heartbeat data.

* * * * *